US011806510B2

(12) United States Patent
Chang et al.

(10) Patent No.: US 11,806,510 B2
(45) Date of Patent: Nov. 7, 2023

(54) SHELL FOR A MEDICAMENT DELIVERY DEVICE

(71) Applicant: SHL MEDICAL AG, Zug (CH)

(72) Inventors: Wen-An Chang, Taoyuan (TW); Hsueh-Yi Chen, Lujhou (TW); Chia-Hsin Su, New Taipei (TW)

(73) Assignee: SHL MEDICAL AG, Zug (CH)

( * ) Notice: Subject to any disclaimer, the term of this patent is extended or adjusted under 35 U.S.C. 154(b) by 451 days.

(21) Appl. No.: 16/951,778

(22) Filed: Nov. 18, 2020

(65) Prior Publication Data
US 2021/0069415 A1 Mar. 11, 2021

Related U.S. Application Data

(63) Continuation of application No. 16/221,356, filed on Dec. 14, 2018, now Pat. No. 10,905,826, which is a (Continued)

(30) Foreign Application Priority Data

Nov. 28, 2013 (SE) .................................... 1351416-1

(51) Int. Cl.
*A61M 5/20* (2006.01)
*A61M 5/31* (2006.01)
*A61M 5/32* (2006.01)

(52) U.S. Cl.
CPC ............ *A61M 5/20* (2013.01); *A61M 5/3129* (2013.01); *A61M 5/3134* (2013.01); (Continued)

(58) Field of Classification Search
CPC .... A61M 5/3129; A61M 5/20; A61M 5/3202; A61M 5/3204; A61M 2005/2006; (Continued)

(56) References Cited

U.S. PATENT DOCUMENTS

| 1,351,461 A | 8/1920 | Beckmann |
| 4,671,408 A | 6/1987 | Raines et al. |

(Continued)

FOREIGN PATENT DOCUMENTS

| CA | 2842376 A1 | 2/2013 |
| EP | 1487517 B1 | 8/2007 |

(Continued)

OTHER PUBLICATIONS

International Search Report and Written Opinion for Int. App. No. PCT/EP2014/075101, dated Feb. 9, 2015.
(Continued)

*Primary Examiner* — Jason E Flick
*Assistant Examiner* — Justin L Zamory
(74) *Attorney, Agent, or Firm* — MCDONNELL BOEHNEN HULBERT & BERGHOFF LLP

(57) ABSTRACT

The present invention relates to a shell assembly for a medicament delivery device, which shell assembly comprises at least one first shell section provided with an entry passage and designed such that at least a major part of a medicament delivery device entered through said entry passage is accommodated inside said at least one first shell section, a closure element operably arranged to said at least one first shell section for closing said entry passage, and fixation elements arranged for fixating said medicament delivery device in relation to said at least one first shell section and said closure element.

19 Claims, 17 Drawing Sheets

Related U.S. Application Data continuation of application No. 15/039,815, filed as application No. PCT/EP2014/075101 on Nov. 20, 2014, now Pat. No. 10,463,793.

(52) U.S. Cl.
CPC ........ *A61M 5/3137* (2013.01); *A61M 5/3202* (2013.01); *A61M 5/3204* (2013.01); *A61M 2005/2006* (2013.01); *A61M 2005/3142* (2013.01); *A61M 2205/58* (2013.01); *A61M 2205/586* (2013.01); *A61M 2205/60* (2013.01); *A61M 2209/06* (2013.01)

(58) Field of Classification Search
CPC ...... A61M 2005/3142; A61M 2205/58; A61M 2205/586; A61M 2205/60; A61M 2209/06
See application file for complete search history.

(56) References Cited

U.S. PATENT DOCUMENTS

| | | | |
|---|---|---|---|
| 5,295,965 | A | 3/1994 | Wilmot |
| 5,709,662 | A | 1/1998 | Olive et al. |
| 6,979,316 | B1 | 12/2005 | Rubin et al. |
| 2001/0011163 | A1 | 8/2001 | Nolan et al. |
| 2009/0005737 | A1 | 1/2009 | Chun |
| 2010/0160894 | A1 | 6/2010 | Julian et al. |
| 2010/0187270 | A1 | 7/2010 | Puglisi |
| 2011/0098647 | A1* | 4/2011 | Jennings ............ A61M 5/2033 604/154 |
| 2011/0137281 | A1* | 6/2011 | Tang ................. A61M 5/30 604/500 |
| 2012/0059319 | A1 | 3/2012 | Segal |
| 2012/0289905 | A1* | 11/2012 | Julian .................... A61M 5/20 604/189 |
| 2012/0302947 | A1 | 11/2012 | Canton et al. |
| 2013/0158475 | A1 | 6/2013 | Xia et al. |
| 2014/0378909 | A1 | 12/2014 | De Rosa et al. |

FOREIGN PATENT DOCUMENTS

| | | |
|---|---|---|
| EP | 1703929 B1 | 10/2009 |
| EP | 1494740 | 12/2009 |
| EP | 1494740 B1 | 12/2009 |
| EP | 2544739 B1 | 4/2018 |
| EP | 3042675 B1 | 12/2020 |
| GB | 2493432 A | 2/2013 |
| JP | 2003-533245 A | 11/2003 |
| JP | 2011-098133 A | 5/2011 |
| JP | 2011-530361 A | 12/2011 |
| JP | 2012-152342 A | 8/2012 |
| JP | 2012-196452 A | 10/2012 |
| RU | 2067004 C1 | 9/1996 |
| WO | 00/69488 A2 | 11/2000 |
| WO | 01/62328 A1 | 8/2001 |
| WO | 02/072181 A2 | 9/2002 |
| WO | 03/077973 A2 | 9/2003 |
| WO | 03/086511 A1 | 10/2003 |
| WO | 2010/098927 A1 | 9/2010 |
| WO | 2011/124633 A1 | 10/2011 |
| WO | 2011/141907 A1 | 11/2011 |
| WO | 2012/085021 A1 | 6/2012 |
| WO | 2012/085585 A2 | 6/2012 |
| WO | 2012/103141 A1 | 8/2012 |
| WO | 2012/127365 A1 | 9/2012 |
| WO | 2013/032389 A1 | 3/2013 |
| WO | 2013/089620 A1 | 6/2013 |
| WO | 2013/135549 A1 | 9/2013 |
| WO | 2013/156346 A2 | 10/2013 |

OTHER PUBLICATIONS

Wright Prefilled Syringe Case [retrieved from the internet on Jun. 13, 2014] http://medicool.com/diabetes/diabetes_injectaid_wrightprefill.php.

\* cited by examiner

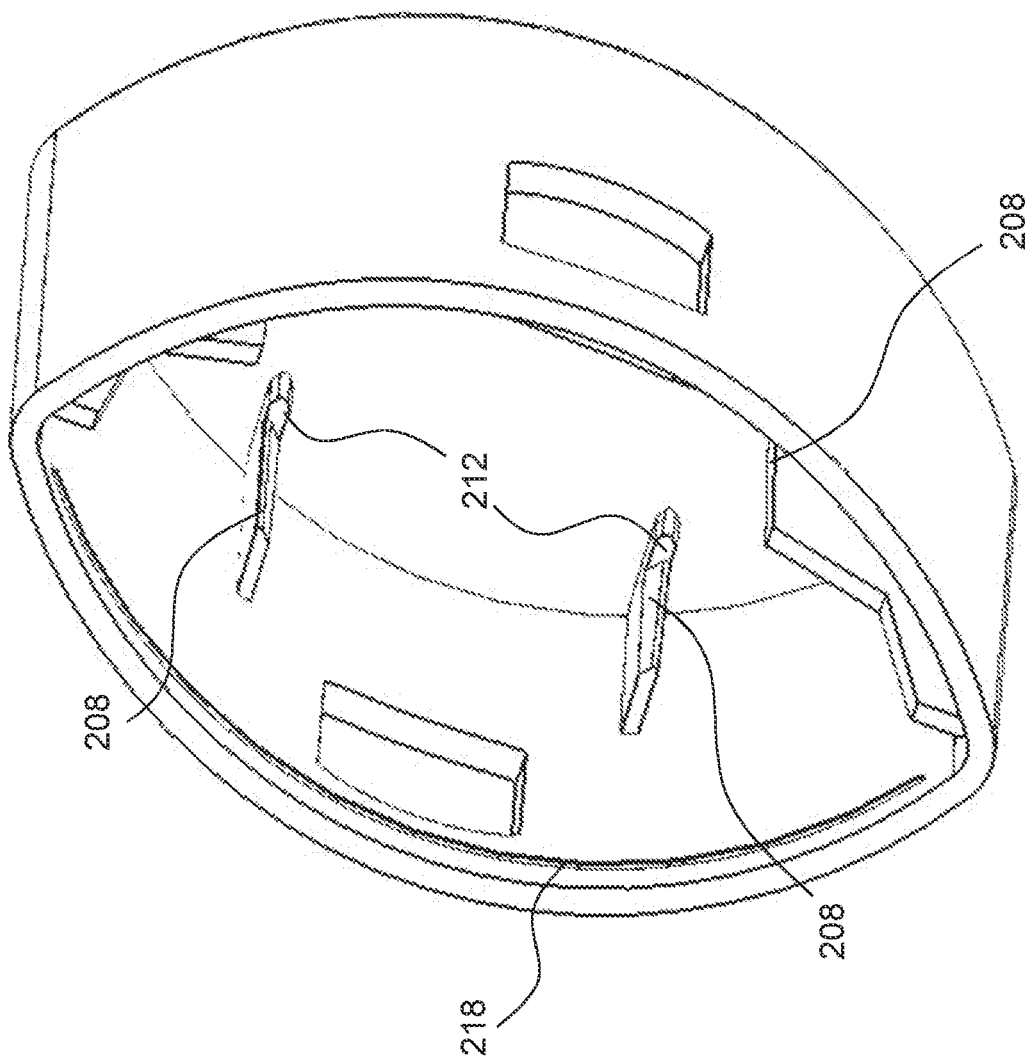

SHELL FOR A MEDICAMENT DELIVERY DEVICE

CROSS REFERENCE TO RELATED APPLICATIONS

The present application is a continuation of U.S. patent application Ser. No. 16/221,356, filed Dec. 14, 2018, which is a continuation of U.S. patent application Ser. No. 15/039,815, filed May 26, 2016, now U.S. Pat. No. 10,463,793, which is a U.S. National Phase application pursuant to 35 U.S.C. § 371 of International Application No. PCT/EP2014/075101 filed Nov. 20, 2014, which claims priority to Swedish Patent Application No. 1351416-1 filed Nov. 28, 2013. The entire disclosure contents of these applications are herewith incorporated by reference into the present application.

TECHNICAL FIELD

The present invention relates to a device to be used together with a medicament delivery device and in particular to a shell assembly that is capable of providing different appearances of the medicament delivery device.

BACKGROUND

There a number of instances where it is desirable to have a certain appearance on a medicament delivery device. This could for instance be the case when a medicament delivery device developed with a number of functions could be used and sold to different end users, i.e. different pharmaceutical companies. The different end users then want to have their own design or profile on the device to distinguish from devices of other companies.

A common solution has generally then been to provide the devices with different types of labels and/or colours in order to give them different appearances. Another solution might also to have different designs on the housing of the medicament delivery devices. This is however quite a major operation because the housing is integrated with functions of the device. Thus a different design then requires alterations of other components and elements of the device in order to maintain the functionality.

Document EP 1 494 740 discloses a medicament delivery device provided with features that are intended to personalize the device in order to make it easier to recognize and to distinguish it from other devices. These features are provided on generally U-shaped elements that are releasibly attached to a handle section of the housing of the device. The U-shaped elements are arranged with features that possess tactile properties such as soft materials, heat generating materials, grip enhancing materials, materials formed with a contour of a hand, etc. The elements may further be arranged with information regarding the user, as well as incorporating metering means such as thermometers, digital watches, blood sugar meter etc.

The U-shaped personalization elements will work well for distinguishing individual devices between users. However, the overall shape and appearance of the medicament delivery device is not altered with different elements. Thus for pharmaceutical companies demanding medicament delivery devices with unique appearances clearly distinguishable from competitor's devices, a mere change of a grip portion will not be sufficient.

There is thus a demand for medicament delivery devices that may be provided with different appearances based on the same basic functionality design.

SUMMARY

In the present application, when the term "distal part/end" is used, this refers to the part/end of the device, or the parts/ends of the members thereof, which under use of the device is located the furthest away from the medicament delivery site of the patient. Correspondingly, when the term "proximal part/end" is used, this refers to the part/end of the device, or the parts/ends of the members thereof, which under use of the device is located closest to the medicament delivery site of the patient.

The aim of the present invention is to remedy the drawbacks of the state of the art devices. This aim is solved by a device for a medicament delivery device comprising the features of the independent patent claim. Preferable embodiments of the inventions form the subject of the dependent patent claims.

According to a main aspect of the invention, it comprises a device for a medicament delivery device. The device comprises a shell provided with an entry passage and is designed such that at least a major part of a medicament delivery device entered through the entry passage is accommodated inside said shell.

With major part is to be understood that the medicament delivery device is mainly hidden inside the shell such that it is the shell that creates the overall appearance of the device with only a small addition of the medicament delivery device. In order to accommodate the medicament delivery device inside the shell, a suitable entry passage may been created, facilitating the assembly of the device. It is of course feasible to provide the shell as two or more parts that are attached to each other after introduction of the medicament delivery device. For example the shell may be in two halves that are glued or welded together when the medicament delivery device is in place.

When the shell is arranged with an entry passage, preferably the device may further be arranged with a closure element operably arranged to said shell for closing said entry passage. The closure element is preferably arranged such that it contributes to the overall appearance of the device as well as ensuring that the medicament delivery device is firmly held inside the shell.

Regarding ensuring that the medicament delivery device is held firmly inside the shell, preferably fixation elements may be arranged for fixating said medicament delivery device in relation to said shell and said closure element. This may be an important factor since many users are not comfortable with devices that make rattling noises when used. Thus, it is an advantage if the medicament delivery device is held firmly by the shell by fixation elements. It is also an advantage if the medicament delivery device is held against rotation since some devices require a turning action when a medicament delivery member is attached, such as screw threads on an injection needle.

In that respect, it may be an advantage if the device comprises a passage through which at least a medicament delivery member of said medicament delivery device may protrude. This design facilitates the attachment of a medicament delivery member and the subsequent dose delivery. The passage may also be used for other elements and functions of the medicament delivery device. For example, the medicament delivery device may include an actuator that activates the medicament delivery device when pressed against a dose delivery site. Such an element my for example comprise a medicament delivery member guard, that is arranged movable in the longitudinal direction of the device.

According to one feasible solution, the passage may be arranged in the closure element. This design may facilitate the assembly of the device together with the medicament delivery device. The device may further preferably be arranged with first locking elements operably arranged to lock the closure element to the shell. In this respect, the first locking elements may be arranged releasable and if so, they may comprise any of threads, bayonet connection, snap-in elements.

As an alternative, the locking elements may be arranged non-releasable and if so, glue may be used as attachment media. Also the contact surfaces may be exposed to heat such that the material melts and the components are bonded together.

Apart from the first locking elements, the device may further comprise second locking elements operably arranged to lock said closure element to said medicament delivery device. With this solution, a very sturdy fixation of the medicament delivery device in relation to the shell is obtained in that the medicament delivery device is attached to the closure element and then the closure element is attached to the shell. This may also be an advantage when assembling the medicament delivery device and the shell because the closure element may firstly be attached to the medicament delivery device and then the assembly is introduced into the shell where the closure element is attached to the shell.

As with the first locking elements also the second locking elements may be arranged releasable and may comprise any of threads, bayonet connection, snap-in elements. As an alternative, the second locking elements may be arranged non-releasable.

According to one favourable solution, the closure element may preferably comprise a second shell section. With this solution the shell is made of two sections that interact and cover the medicament delivery device. This provides the opportunity to divide a shell in at least two sections, and perhaps more, that interact with each other to form a complete shell surrounding the medicament delivery device.

In that aspect the at least first and said second shell sections comprise third attachment elements operably arranged to connect the shell sections to each other. The third attachment elements may preferably be suitable connection elements that are capable to connect the shell sections together in a positive and secure way.

Depending on the type of device and the intended application, the third attachment elements may comprise snap-in elements or they may be arranged non-releasable. The snap-in elements may have a number of designs that provide a locking function between the shell sections.

According to another aspect of the embodiment, the at least first and second shell sections may comprise joints operably arranged to movably connect the shell sections such as to open and/or close the shell. With this solution, the shell sections are connected to each other via the joints, providing an easy handling of the shell sections when a medicament delivery device is placed inside the shell sections and they are brought together.

The joints may be of a number of different types, such as hinges. These hinges may be a number of discrete sections or a longer continuous or piano hinges. Different materials may be used for creating the hinges, where they may be integrated in the shell sections. In that aspect the joints may also comprise flexible bridges that may be formed by the same material as the shell sections.

According to a further aspect of the invention, the closure element may be integral with said medicament delivery device. This solution reduces the number of components in that the closure element is an integrated part of the medicament delivery device. This also facilitates the assembly of the shell section with the medicament delivery device.

In this respect, the closure element may be formed when molding the medicament delivery device. On the other hand, the closure element may be fixedly attached to the medicament delivery device by e.g. gluing or plastic welding before assembly with the first shell section.

Preferably this variant may comprise first attachment elements operably arranged to lock said closure element and thereby said medicament delivery device to said first shell section. The first attachment elements may either be arranged releasable or non-releasable.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which FIG. 17 is a detailed view of a shell section of the device of FIG. 14.

DETAILED DESCRIPTION

Figure 1:
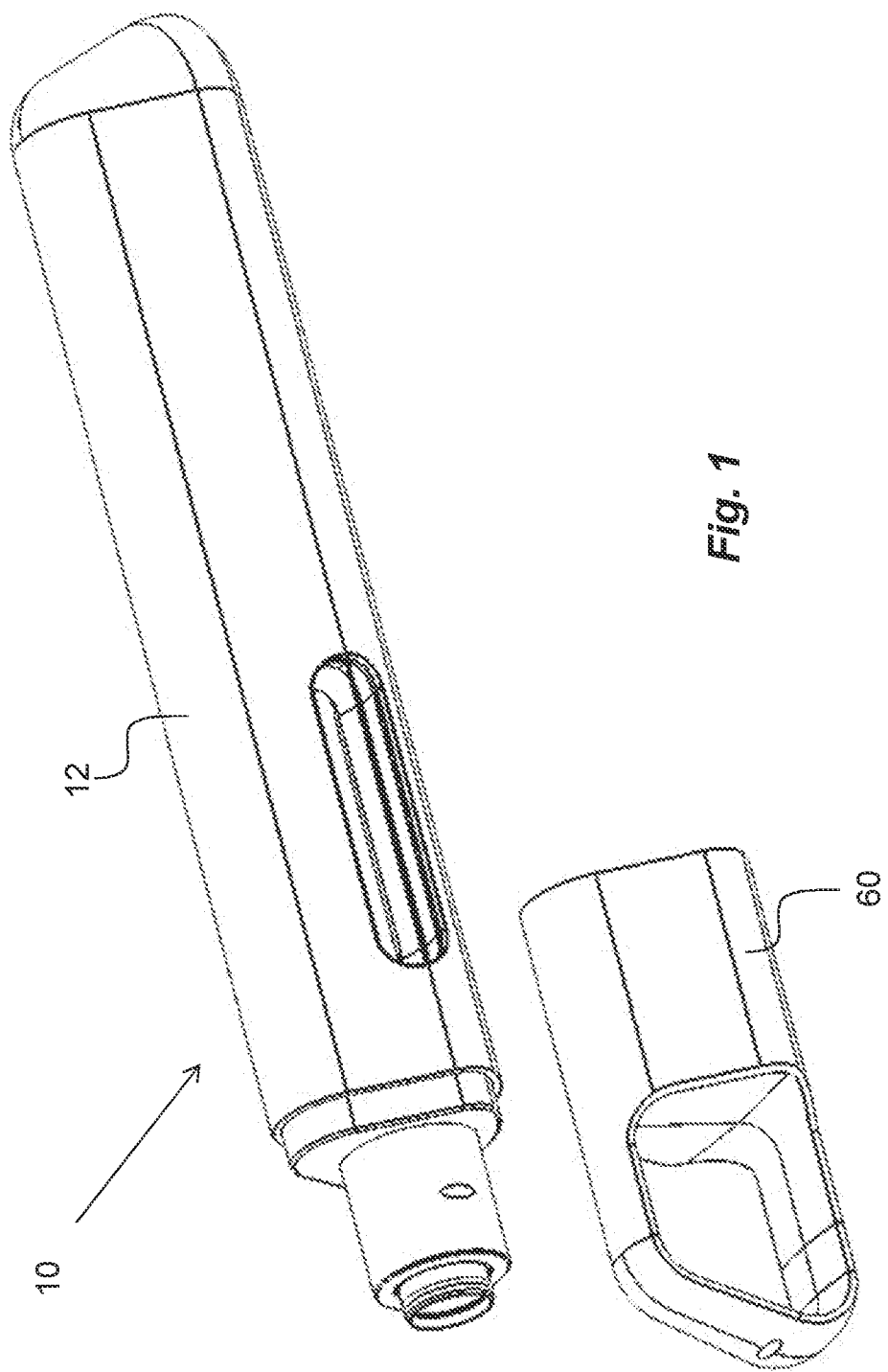
FIG. 1 is a perspective view of a feasible embodiment of a device for a medicament delivery device.

A feasible embodiment of a medicament delivery device arranged with a device 10 according to the present invention is shown in the drawings. The device 10 as shown comprises a generally tubular first shell section 12 or housing designed and dimensioned to accommodate a medicament delivery device 14, FIG. 2. In that respect, the medicament delivery device 14 could be of a number of designs and contain a number of different functionalities and features. These do not form part of the invention and will thus not be described in detail. The important factor is that the first shell section 12 is capable of accommodating at least a major part of the medicament delivery device 14.

In the embodiment shown the first shell section 12 is arranged with a distally directed end wall 16. The end wall 16 could either be integrally made with the first shell section 12 or could be a separate component attachable to the shell. In that respect there are a number of methods of attaching components to each other, either releasable or fixed. For example fastening components could be used, such as threads, bayonet connections, snap-in fittings etc. The components could also be glued or welded to each other. The proximal end of the shell is further arranged with an entry passage 18, FIG. 2, through which the medicament delivery device 14 may be inserted into the first shell section 12.

Figure 3:
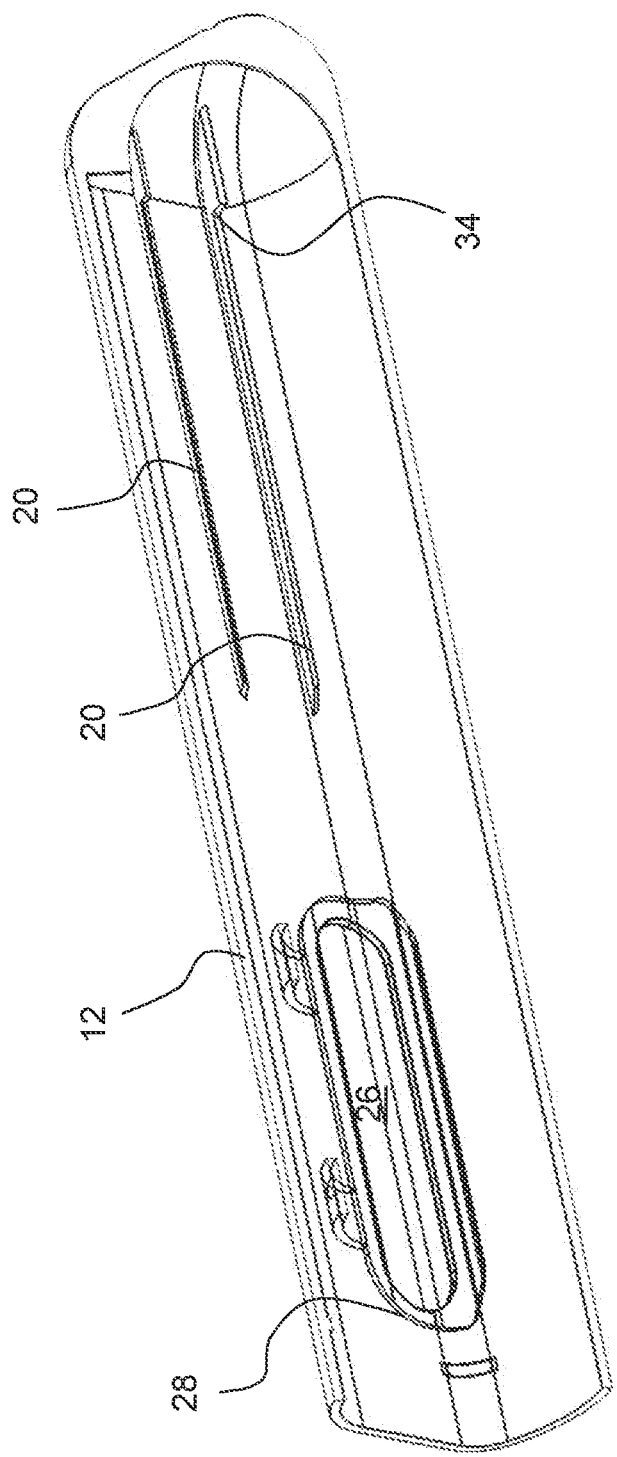

In order to fit the medicament delivery device 14 in a stable manner inside the first shell section 12, a number of fixation elements are provided between the shell and the medicament delivery device that interact with each other. One type of fixation elements may be protrusions or guides. For example, the inner surface of the first shell section 12 may be arranged with longitudinally extending ribs 20, as seen in FIG. 3. These ribs 20 are designed and arranged such that they come in contact with outer surfaces of the medicament delivery device 14 when inserted into the first shell section 12. Preferably these fixation elements in the form of ribs 20 are capable of preventing linear movement between the first shell section 12 and the medicament delivery device 14 both in the longitudinal direction and transversal direction as well as rotating movement.

Figure 2:
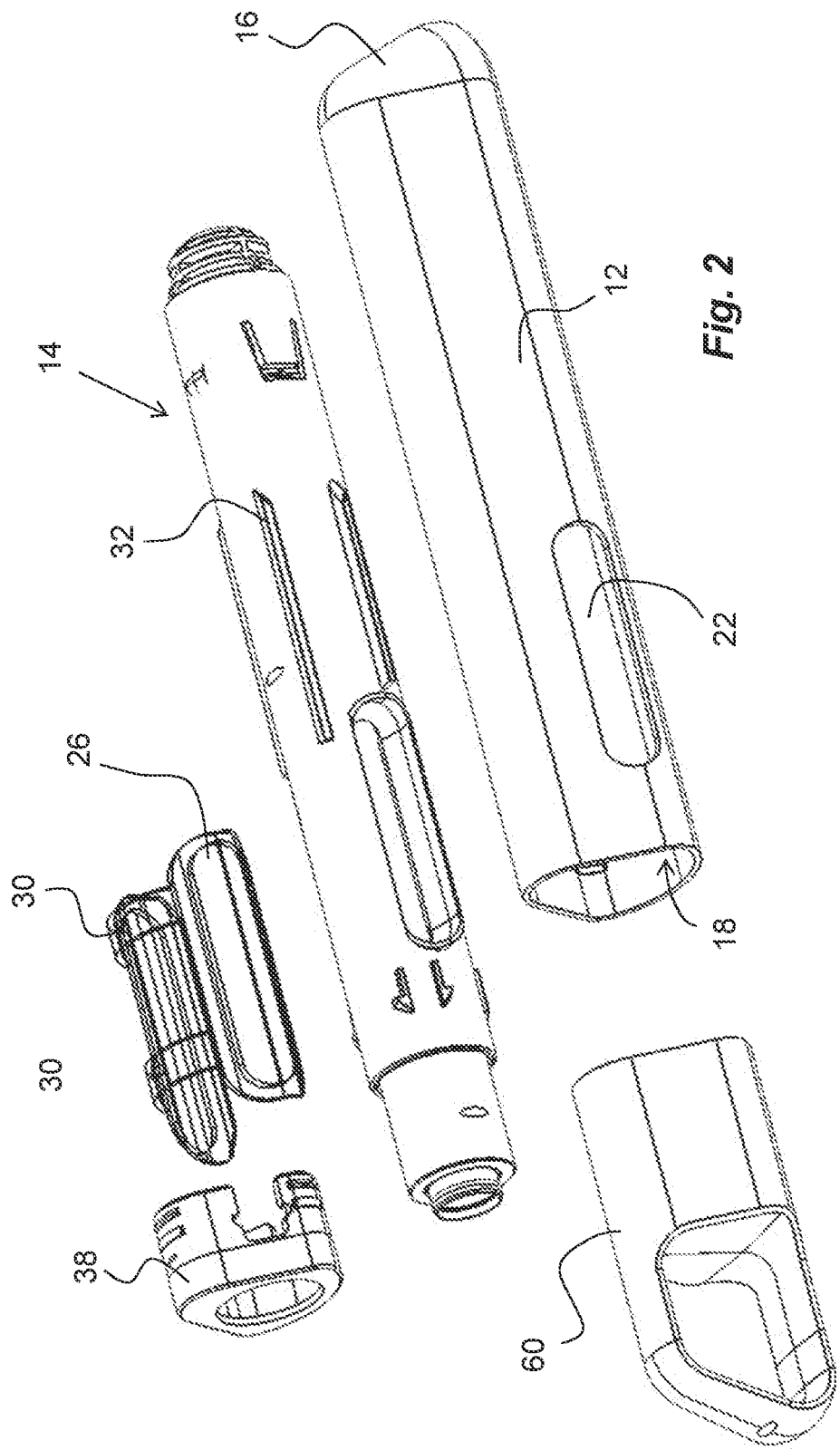
FIG. 2 is an exploded view of the device of FIG. 1, FIGS. 3-8 are detailed views of elements comprised in the device of FIG. 1.
Figure 4:
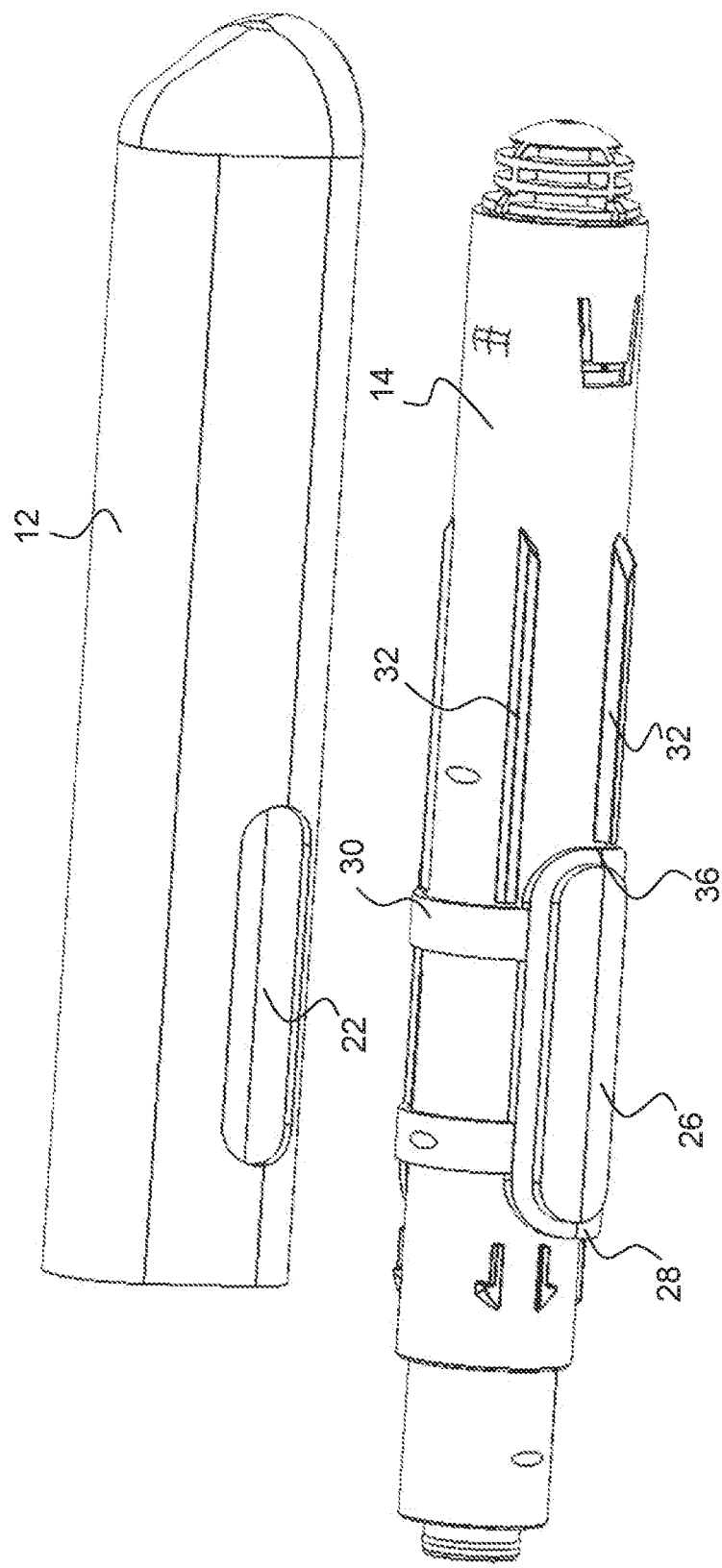
Figure 8:
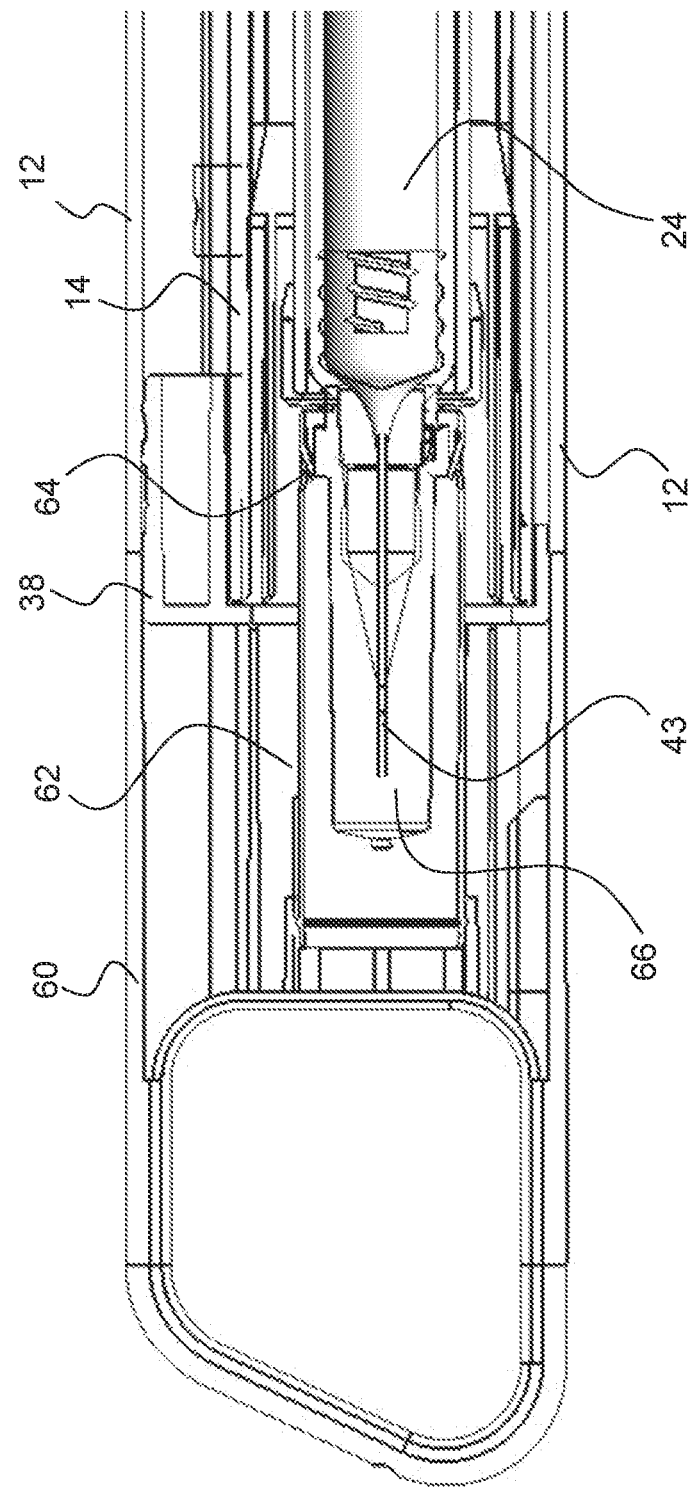
Figure 9:
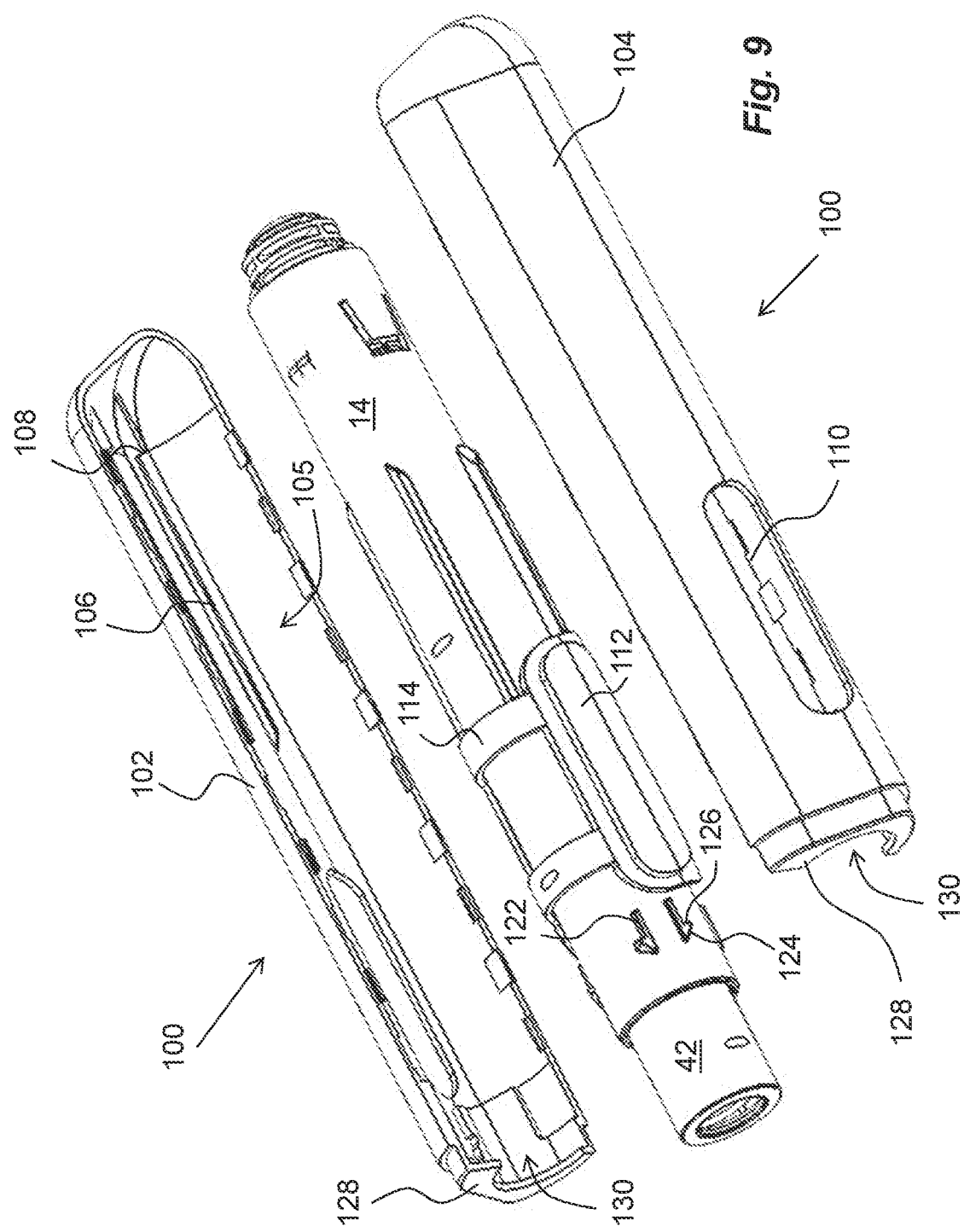
FIG. 9 is an exploded view of a variant to the device of FIG. 1, FIGS. 10-12 are detailed views of elements comprised in the device of FIG. 9.
Figure 10:
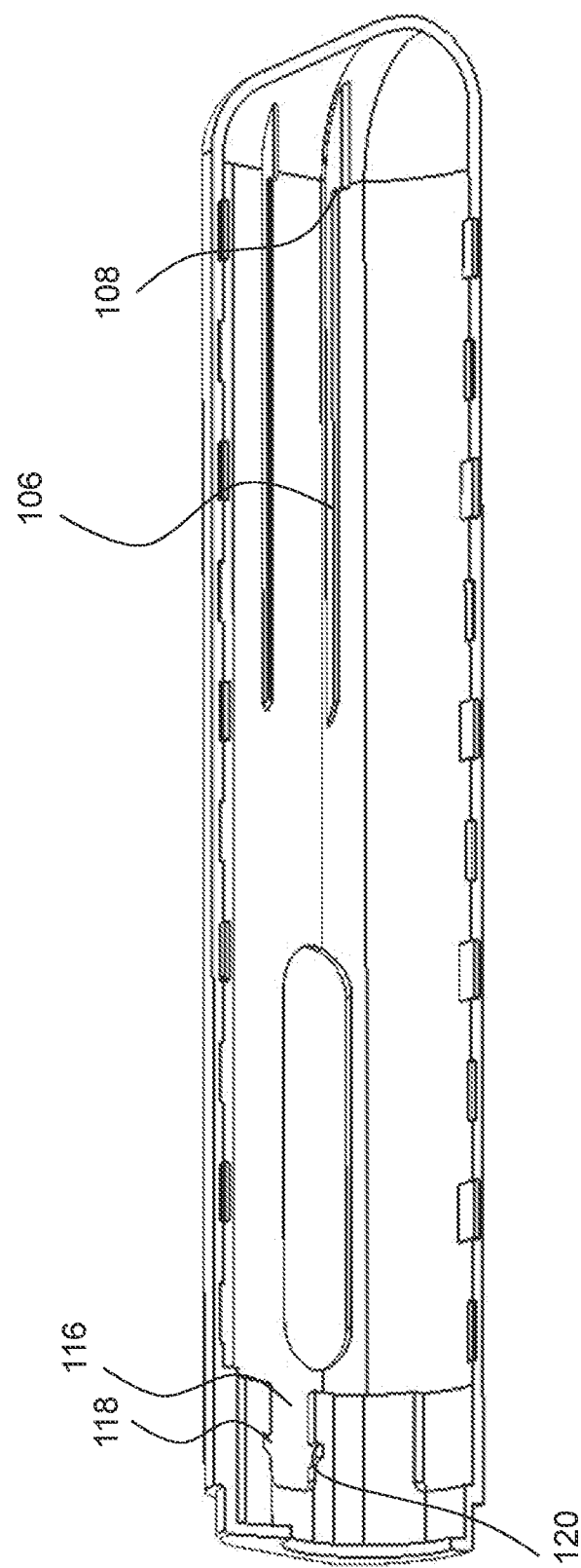

In the embodiment shown the shell is arranged with openings 22, FIGS. 2 and 4, such that a medicament container 24, FIG. 8, in the medicament delivery device 14 may be visible such that the content of the medicament can be viewed by a user. In the embodiment shown the openings 22 are placed on opposite sides of the shell as seen in a transversal direction. The openings 22 are arranged with windows 26, FIGS. 3 and 4, made of a transparent material. Each window 26 is arranged with a circumferential ledge 28, FIGS. 3 and 4, such that when the windows 26 are placed in the openings 22, the ledges 28 engage an inner surface of the first shell section 12 adjacent the openings, FIG. 3. This design ensures that the windows are fixedly placed in the openings. In order to facilitate assembly of the windows 26, two flexible bridges 30 are arranged between the windows 26, FIGS. 2 and 4, which bridges 30 are curved such that they do not interfere with the interior of the first shell section 12. The flexing properties of the bridges 30 enable positioning and retaining of the windows 26 in the openings 22. The thickness of the windows 26 and the design of the medicament delivery device 14 are such that when the medicament delivery device 14 is placed in the shell, it will be in contact with the inner surface of the windows 26, thereby preventing the windows from being pushed into the shell.

Further fixation elements may be arranged. In the embodiment shown, the medicament delivery device 14 may also be arranged with longitudinally extending ribs 32, FIG. 4. These may fixate in the transversal direction but may also prevent movement in the longitudinal direction as well as rotational movement. For example, when the medicament delivery device 14 is pushed into the first shell section 12, the ribs 32 will slide along the inner surface of the windows 26, which is possible due to the elasticity of the first shell section 12. The ribs 32 will then pass the ledge 28 of the windows, and the length of the ribs 32 have been chosen such that when a distally directed surface of the medicament delivery device 14 abuts a proximally directed contact surface 34 of the shell, FIG. 3, proximally directed end surfaces 36 of the ribs 32, FIG. 4, are adjacent distally directed surfaces of the ledges 28 of the windows 26. Thereby the medicament delivery device 14 is locked in the longitudinal direction in relation to the first shell section 12.

Figure 5:
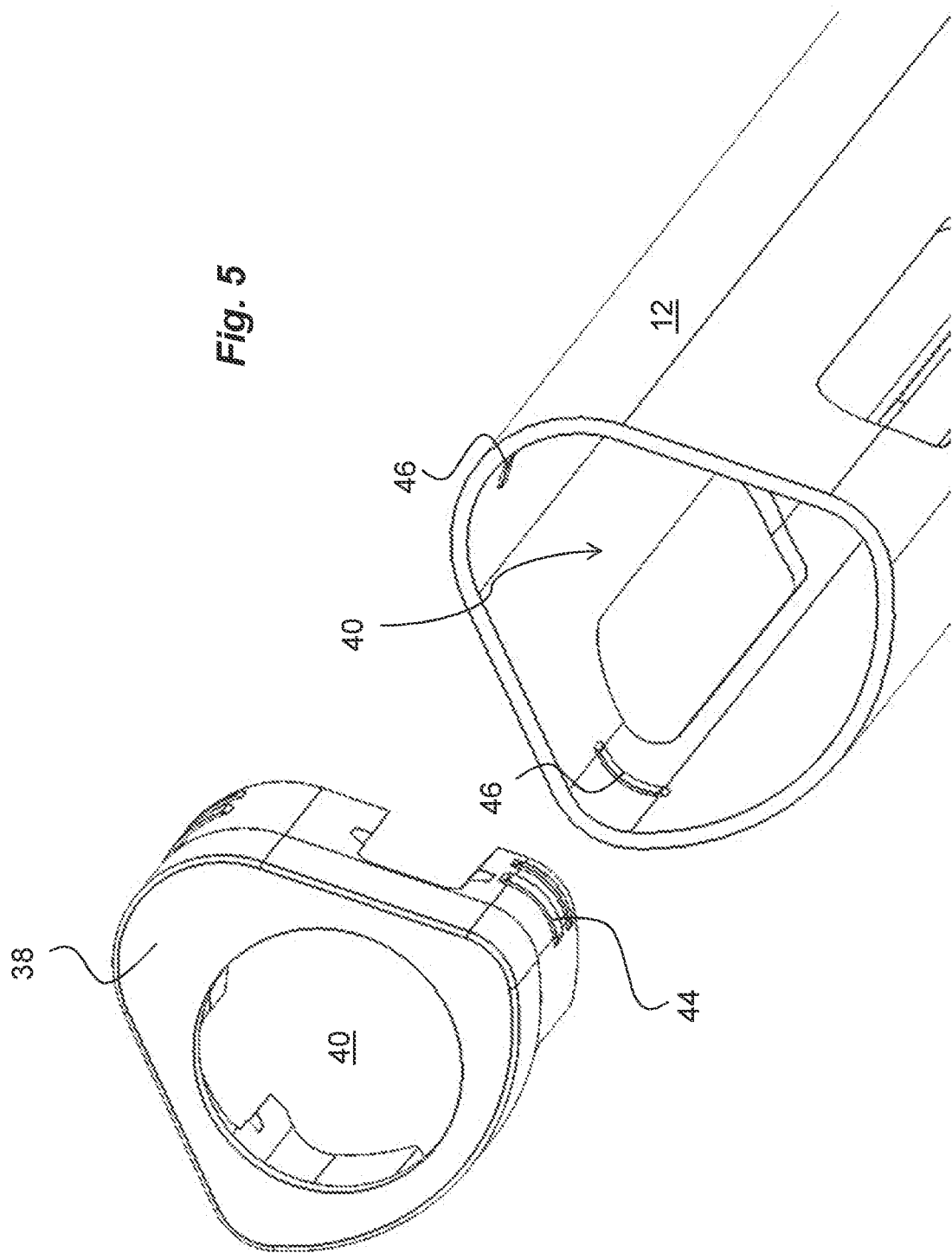

Preferably the device according to the embodiment is arranged with a proximal closure element 38, FIGS. 2 and 5. This may comprise an end cap 38 having a central passage 40 through which a proximal end 42 of the medicament delivery device 14 may protrude, which proximal end may comprise a number of elements. For example the medicament delivery device may be arranged with an attachment element for attaching a medicament delivery member such as an injection needle or the like. As an alternative, the medicament container may be integrated with a medicament delivery member 43, FIG. 8. Also the medicament delivery device may be arranged with an actuator that triggers e.g. a penetration sequence and/or an injection sequence, which actuator may be a medicament delivery member shield. These elements have to be accessible to a user and they preferably extend through the central passage 40.

Figure 6:
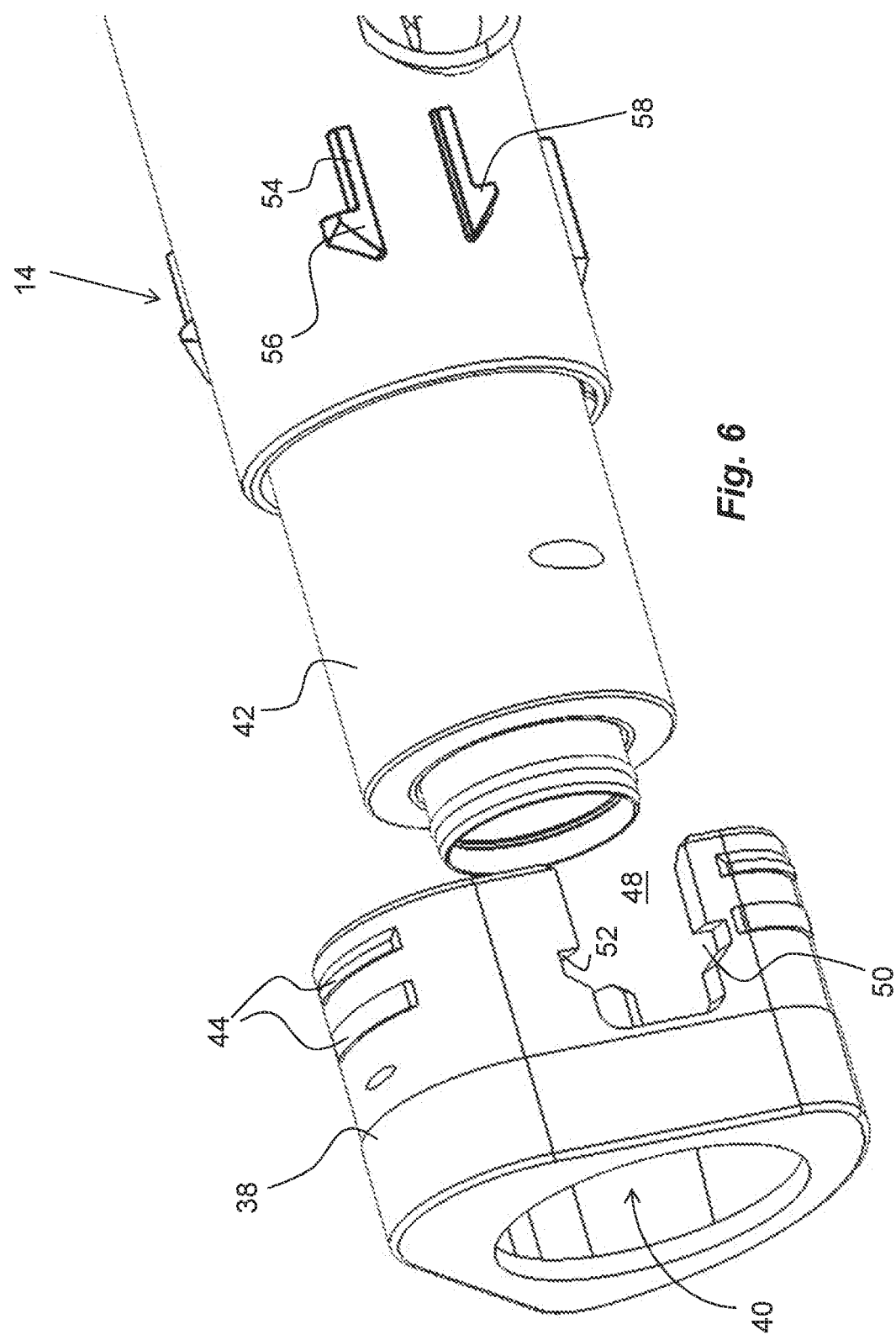

Further the end cap 38 is arranged with a number of first attachment elements for connecting with the shell. In the embodiment shown the first attachment elements are arranged as protrusions or ledges 44, FIGS. 5 and 6, extending transversal to a longitudinal direction. These ledges 44 cooperate with corresponding transversal ledges 46 of the first attachment elements on an inner surface of the first shell section 12 such that when the end cap 38 is pushed into the proximal end of the first shell section 12 the ledges 44, 46 interconnect and lock the end cap 38 to the first shell section 12.

Figure 7:
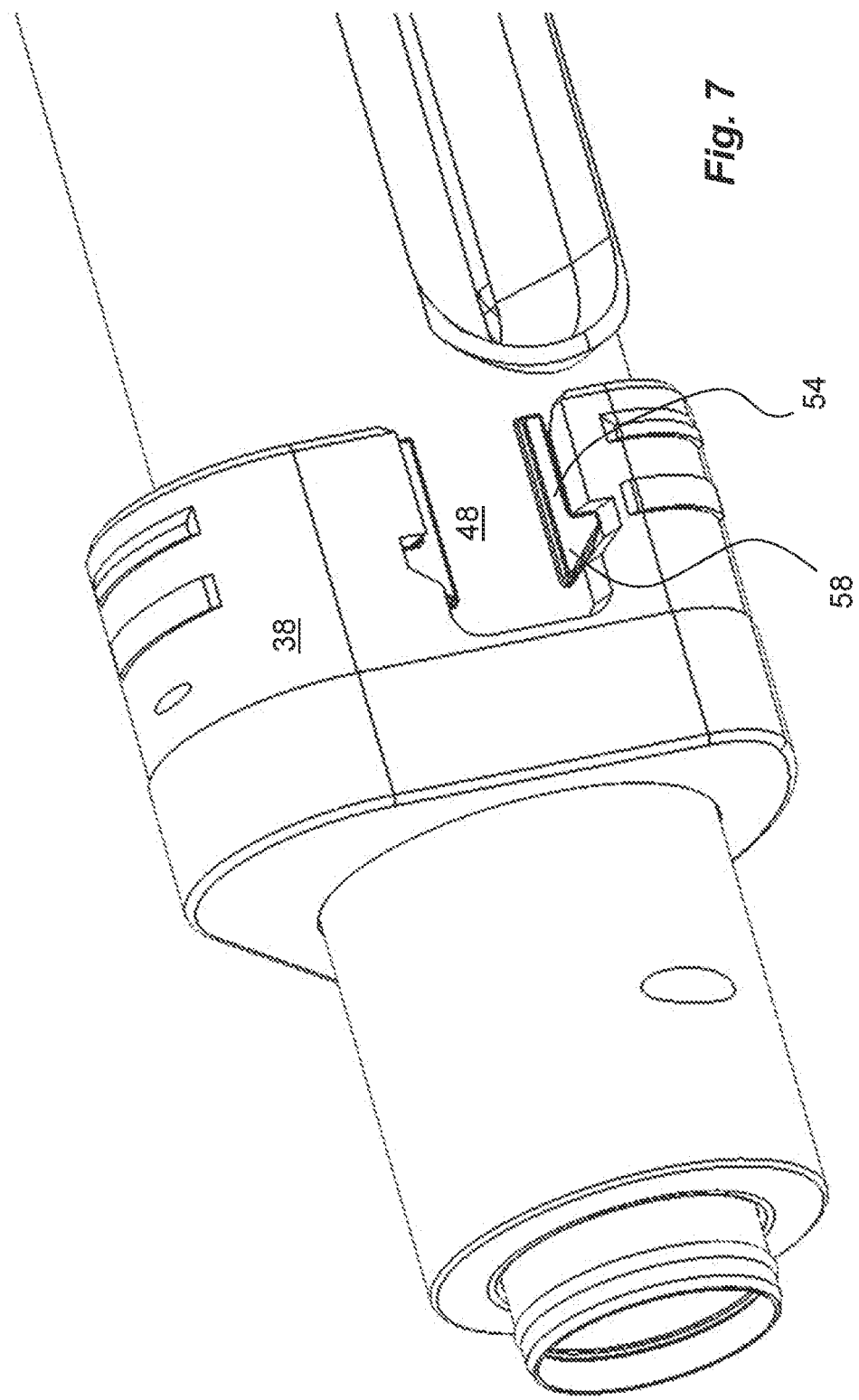

The end cap 38 may further preferably be arranged with second attachment elements to attach the end cap 38 to the medicament delivery device 14, which second attachment elements also may function as further fixation elements. The attachment elements of the end cap may comprise longitudinal slits 48, FIG. 6, arranged with cut-outs 50 on side surfaces of the slits 48, providing proximally directed contact surfaces 52. The medicament delivery device 14 is arranged with corresponding attachment elements. These are arranged as pairs of longitudinally extending ledges 54 having a distance generally corresponding to the width of the slits 48. A proximal end of the ledges 54 is arranged with a wedge-shaped protrusion 56 designed to fit into the cut-out 50 of the side surfaces of the slits 48, such that a distally directed surface 58 of the wedge-shaped protrusion 56 will be in contact with the proximally directed contact surface 52 of the cut-out 50, FIG. 7. With this design, the medicament delivery device will be locked to the end cap 38 both in the longitudinal direction as well as in the rotational direction.

The device may further also be arranged with a protective cap 60, FIGS. 1 and 8, arranged to fit onto the proximal end of the first shell section 12 and the end cap 38, thereby protecting the proximal end 42 of the medicament delivery device 14. The protective cap 60 may further be arranged with removal elements capable of removing for example a needle sheath. In the embodiment shown the removal element comprises a generally tubular remover element 62, FIG. 8, attached to the protective cap 60 and arranged with inwardly inclined grip members 64 capable of gripping into the surface of a needle sheath 66 surrounding an injection needle 43.

FIGS. 9 to 12 show a variant of the device described above. Here a shell 100 comprises a first 102 and a second 104 shell section. In the embodiment shown, the sections are designed as halves having generally the same size. It is however to be understood that one of the halves could be larger and the other half could be smaller. Also, it is to be understood that one of the sections 104 may be regarded as closure element for closing the shell around a medicament delivery device 14 as described, whereby the opening 105, FIG. 9, of the first shell section 102 may be regarded as entry passage, into which opening 105 the medicament delivery device 14 may be placed.

Each shell section is arranged with fixation elements 106 on their inner surfaces, as well as contact surfaces 108. These fixation elements and contact surfaces are arranged to be in contact with, and fixate, a medicament delivery device placed inside the shell. Each shell section is further arranged with openings 110 in which windows 112 can be inserted. As with the previous device, the windows are connected to each other with bridges 114. The inner surface of each first 102 and second 104 shell section is further arranged with third attachment elements to attach the shell to the medicament delivery device 14, which third attachment elements also may function as further fixation elements. As with the previous variant, the attachment elements of the shell sections may comprise longitudinal slits 116, FIG. 10, arranged with cut-outs 118 on side surfaces of the slits 116, providing proximally directed contact surfaces 120.

As described above, the medicament delivery device 14 is arranged with corresponding attachment elements. These are arranged as pairs of longitudinally extending ledges 122 having a distance generally corresponding to the width of the slits 116. A proximal end of the ledges 122 is arranged with a wedge-shaped protrusion 124 designed to fit into the cut-out 118 of the side surfaces of the slits 116, such that a distally directed surface 126 of the wedge-shaped protrusion 124 will be in contact with the proximally directed contact surface 120 of the cut-out 118, FIG. 10. With this design, the medicament delivery device will be locked to the shell 100 both in the longitudinal direction as well as in the rotational direction. Each shell section is further arranged with a proximal wall section 128, FIG. 9. The wall sections are arranged with cut-outs 130 that form a central passage when the shell sections are joined, through which central passage a proximal end 42 of the medicament delivery device 14 may protrude.

Figure 11:
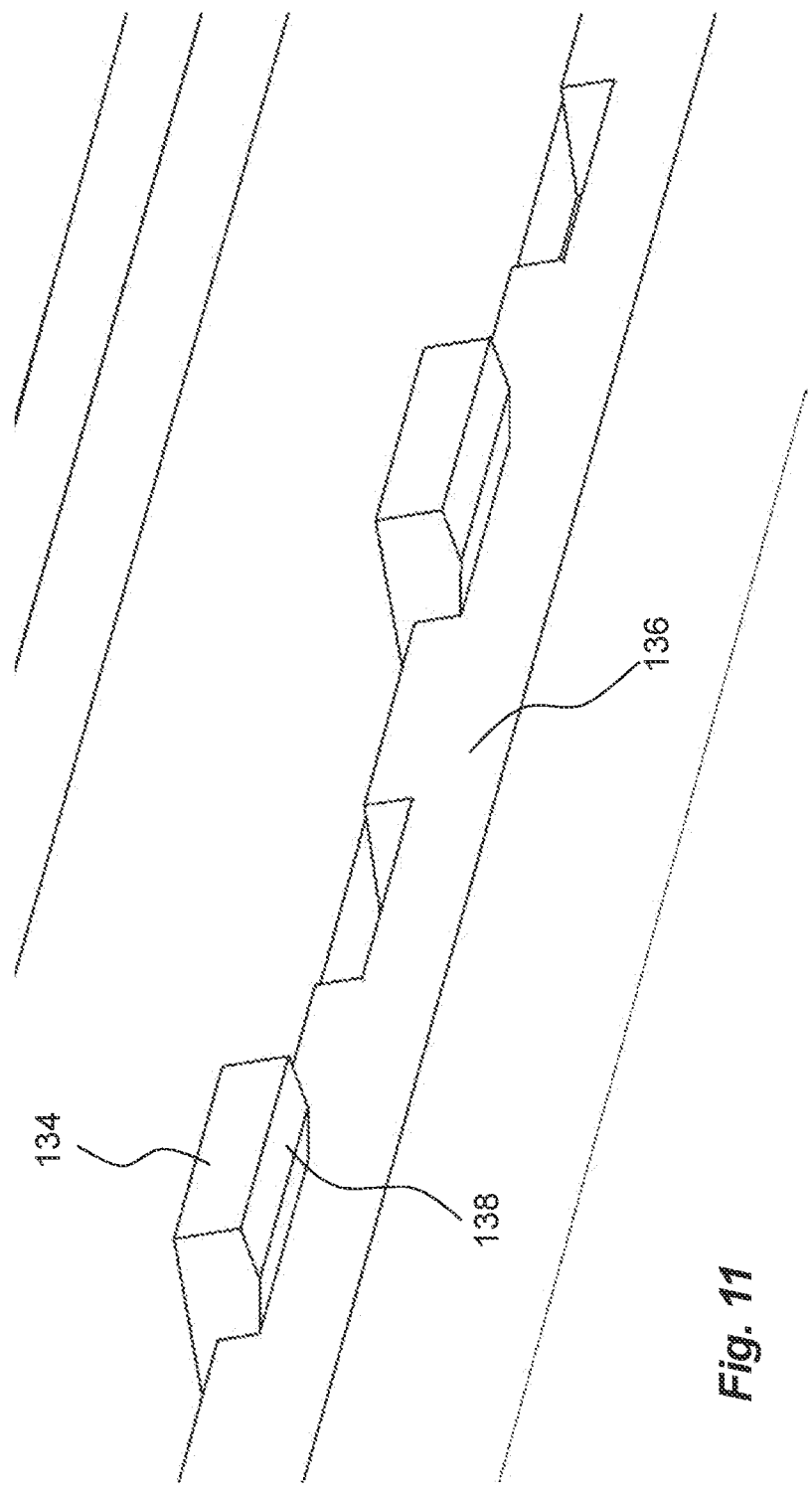
Figure 12:
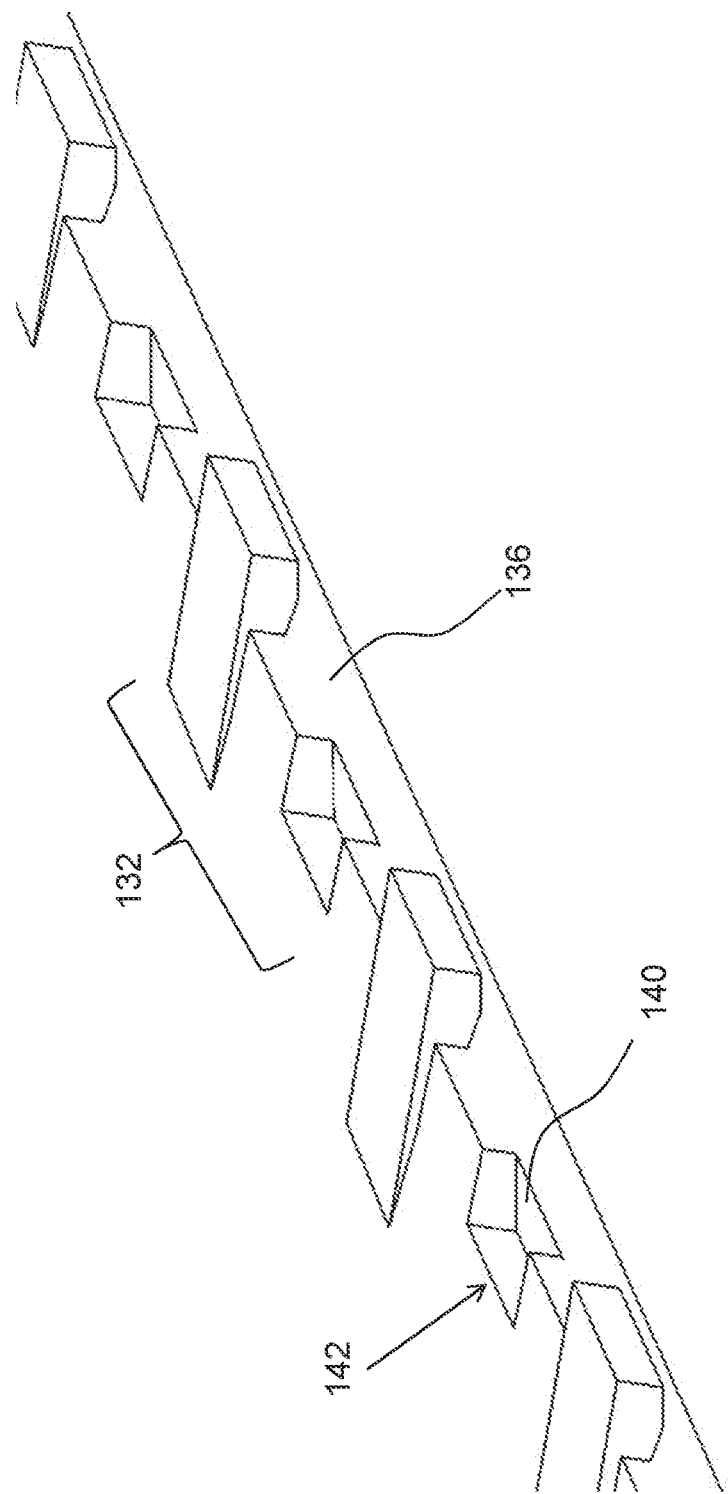

The first 102 and the second 104 shell sections are further arranged with attachment elements 132, FIGS. 11-12. In the embodiment shown, the attachment elements comprise a number of protrusions 134 extending from a contact surface 136 on each shell section. The protrusions are arranged with inclined surface 138, which surfaces 138 are intended to cooperate with inclined surfaces 140 on a number of seats 142, where the position and number of seats 142 correspond to the position and number of protrusions 134. Thus, when the first 102 and the second 104 shell sections are pushed together with the contact surfaces 136 facing each other, the protrusions will fit into the seats whereby the inclined surfaces 138, 140 interact to lock the shell sections to each other with the contact surfaces 136 abutting each other.

Figure 13:
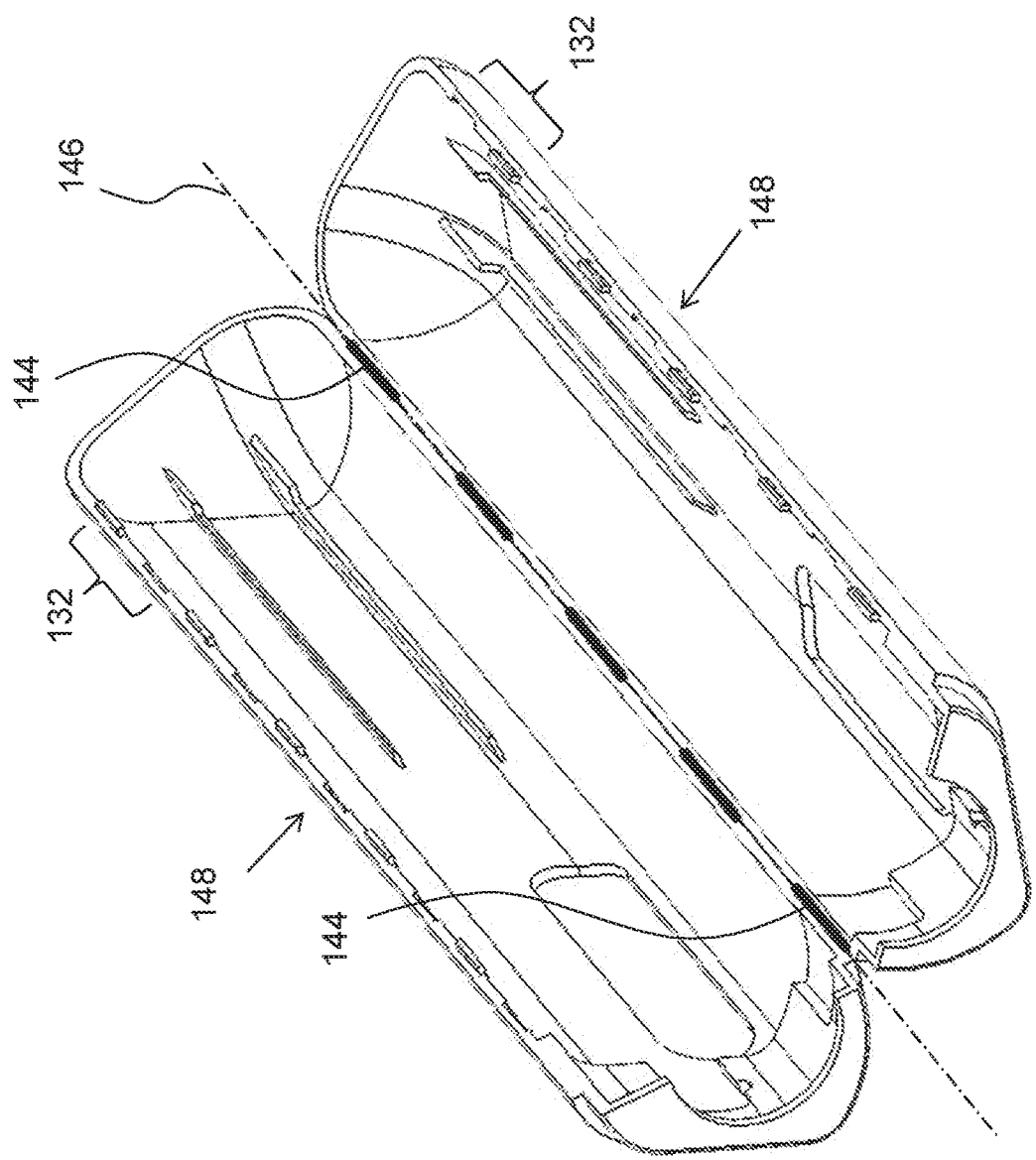
FIG. 13 is a detailed view of an alternative to the device of FIG. 9.

FIG. 13 shows a variant of the device of FIGS. 9 to 12. Here the first 102 and the second 104 shell sections are joined to each other along a long side of each half with joints 144. The joints 144 are arranged to allow turning of the shell sections in relation to each other along a joint axis 146. The joints 144 may be hinges of a conventional design such as continuous or piano hinges of plastic or metal or combinations thereof. There could also be discrete hinge sections as shown in FIG. 13. Further, the joints 144 may be arranged as bridges of the same material as the shell halves, which bridges are so flexible as to function as hinges when the shell sections are turned in relation to each other. The free long sides 148 of the shell sections may be arranged with appropriate attachment elements 132 for connecting the shell sections when the shell is closed, such as those described above.

Further, as described with the first variant of the device, the latter variants may also be provided with protective caps fitting onto the proximal ends of the shells.

FIGS. 14 to 17 show a further variant of the device described above. It comprises a generally tubular first shell section 200 provided with a distal end wall 202 that could either be integral with the first shell section or a separate component attachable to the first shell section. The proximal end of the first shell section 200 is arranged with an entry passage 204, FIG. 15, through which a medicament delivery device 14 may be inserted into the first shell section.

The inner surface of the first shell section is arranged with a number of fixation elements designed and arranged to fit the medicament delivery device 14 in a stable manner inside the first shell section 200. In the variant shown, the fixation elements comprise longitudinally extending ribs 208, FIGS. 16 and 17, that interact with the outer surface of the medicament delivery device 14 such as to prevent any movement. Also the ribs 208 may interact with longitudinally extending ribs 210, FIGS. 15 and 16, on the outer surface of the medicament delivery device 14 such as to prevent rotation of the medicament delivery device 14 inside the first shell section 200, as can be seen in FIG. 16. The ribs 208 are further arranged with ledges or end surfaces 212, FIG. 17, that interact with distally directed surfaces of the medicament delivery device for limiting movement in the longitudinal direction, as seen in FIG. 16.

Figure 14:
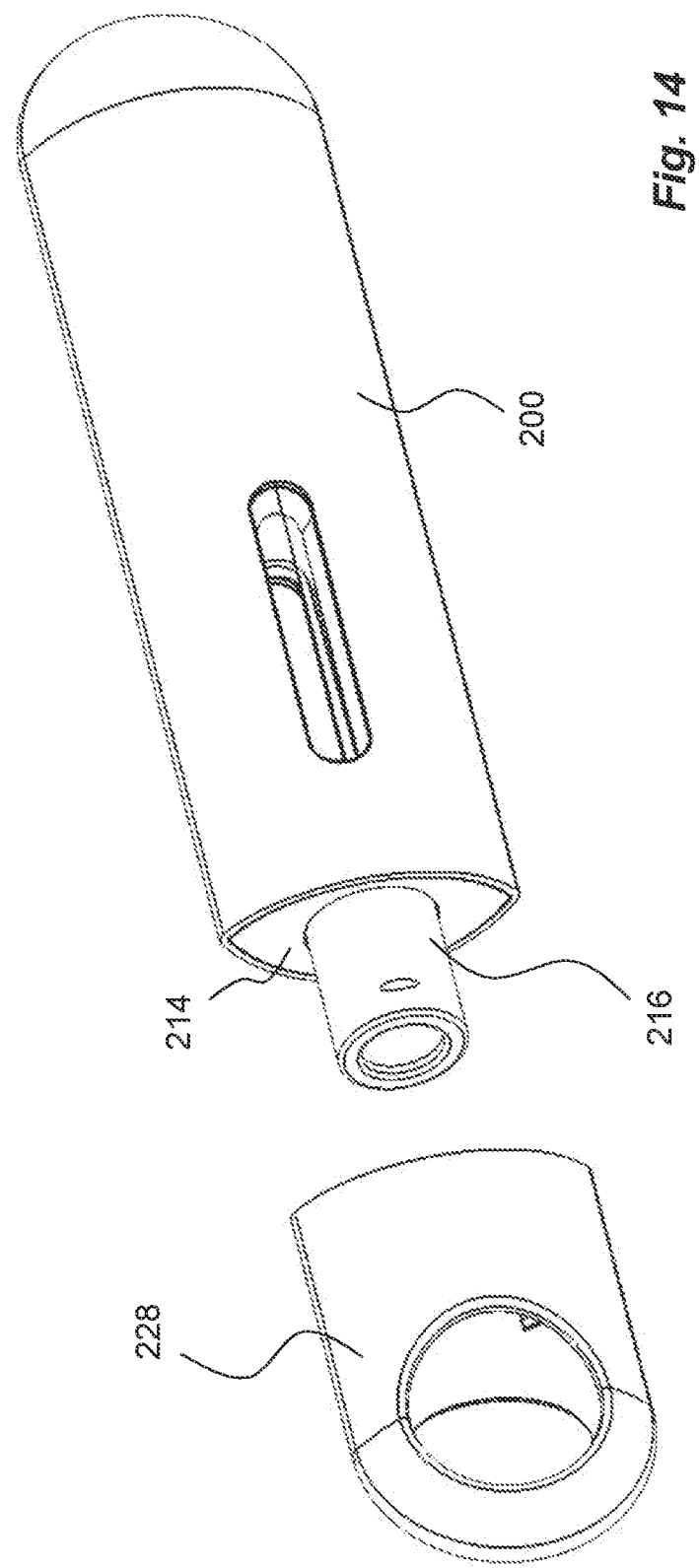
FIG. 14 is a perspective view of a further variant of the device.
Figure 15:
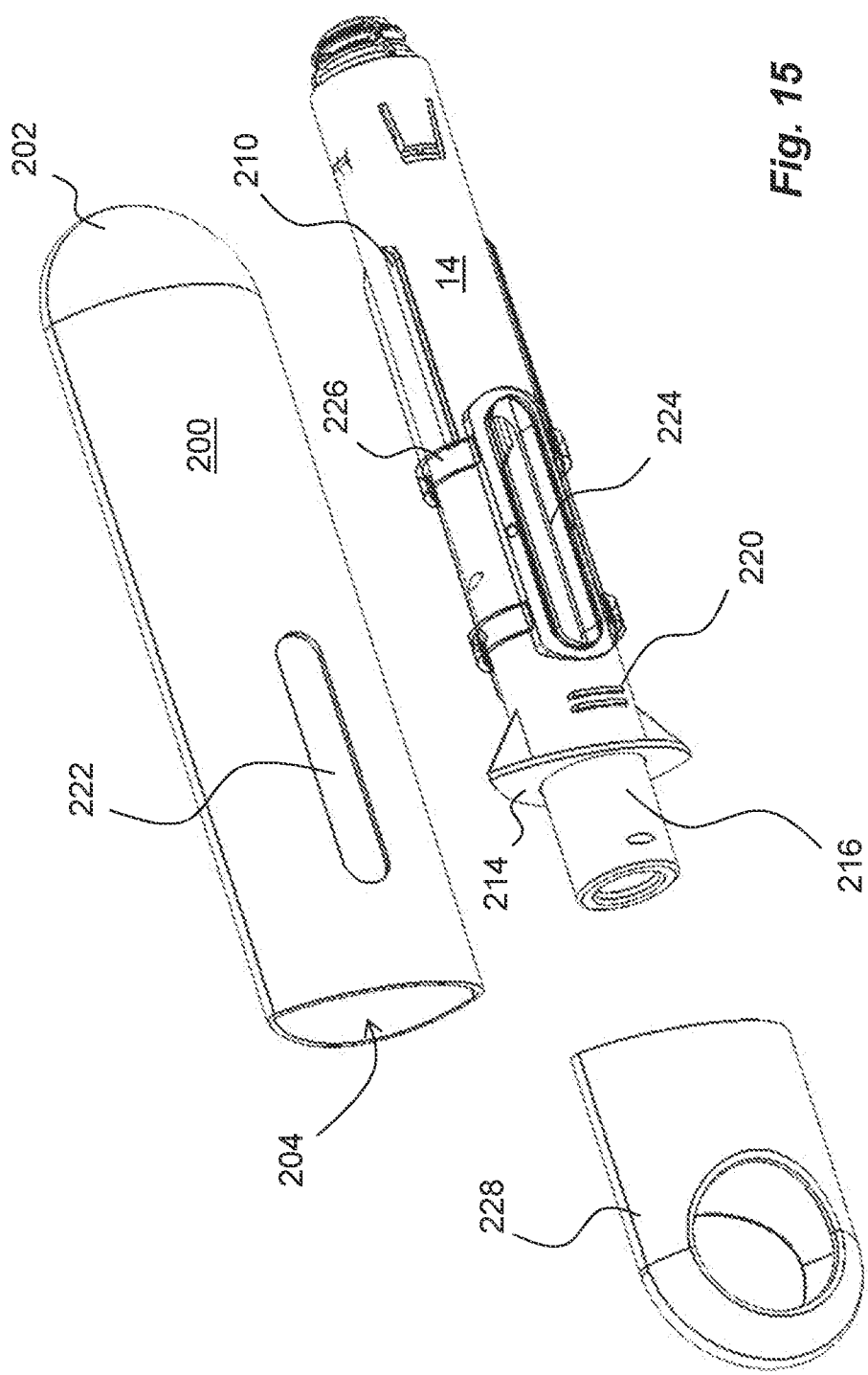
FIG. 15 is an exploded view of the variant of FIG. 14.
Figure 16:
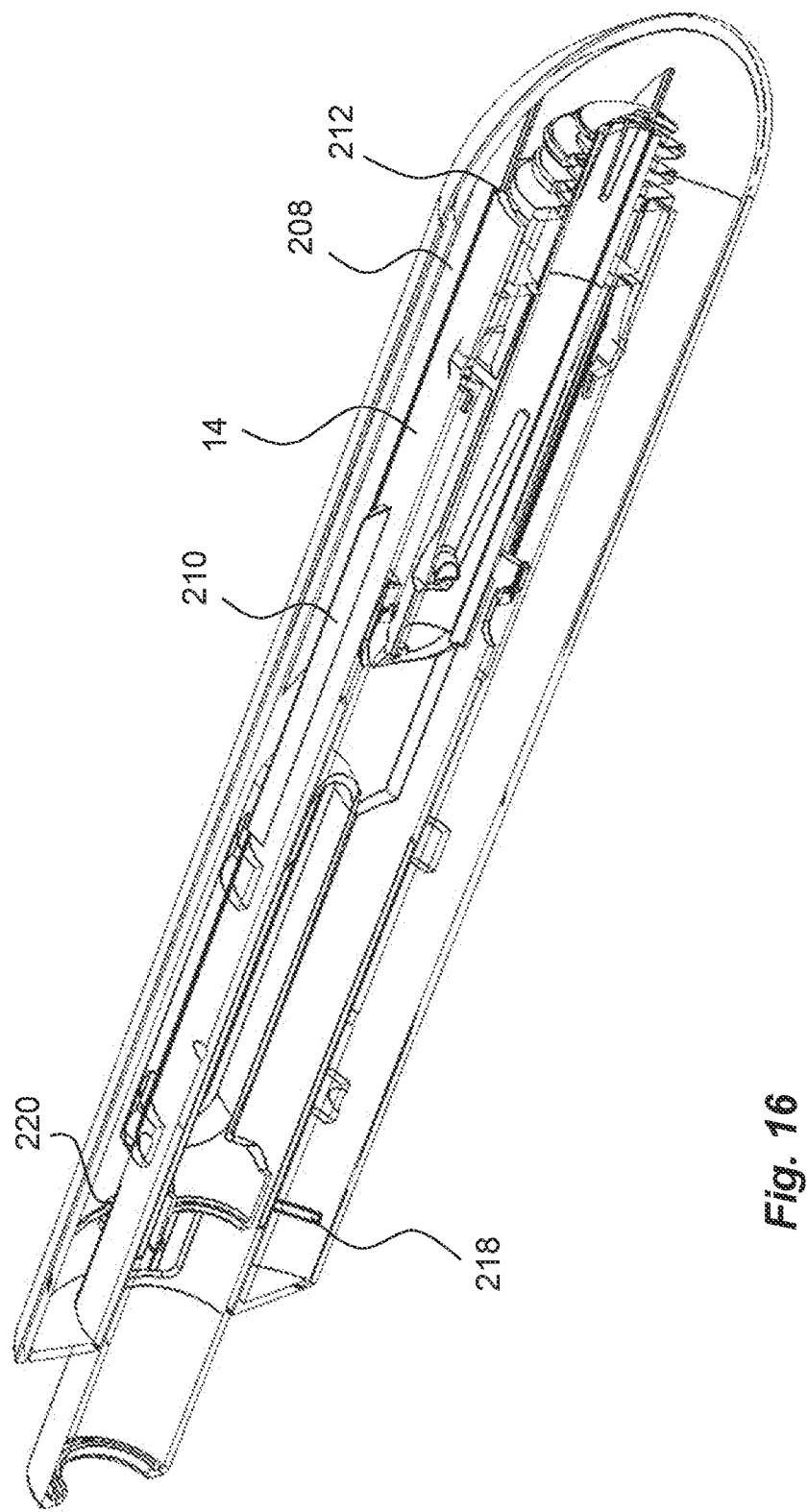
FIG. 16 is a cross-sectional view of the device of FIG. 14.

In the variant described, a closure element 214 of the passage 204, FIGS. 14 and 15, is arranged as an integral part of the medicament delivery device 14. The closure element 214 is shaped to fit into the passage 204 as seen in FIG. 14, such that when the medicament delivery device is positioned in the first shell section, a proximal end 216 of the medicament delivery device protrudes in the proximal direction, in the same manner as described above. The attachment elements between the medicament delivery device 14 and the first shell section 200 may comprise a number of different solutions such as snap in connections, glue, welding and the like. In the embodiment shown the inner surface of the first shell section 200 is arranged with a ridge 218, FIG. 18, extending generally transversal to the longitudinal direction L. The ridge 218 is intended to interact with two parallel ridges 220 arranged on the outer surface of the medicament delivery device 14, FIG. 15, and extending generally transversal to the longitudinal direction L.

When the medicament delivery device is pushed into the first shell section it will abut the end surfaces 212 while the ridge 218 on the first shell section will be positioned between the two parallel ridges 220, thereby locking the medicament delivery device with the first shell section as seen in FIG. 16. In the same manner as the above variants, the present variant is arranged with openings 222 on the first shell section, in which windows 224 may be positioned. The windows are preferably interconnected by bridges 226 as described above.

Further, as with the previous variants, a protective cap 228, FIG. 14, may be removably arranged to the proximal end of the medicament delivery device and the first shell section, as described above.

It is to be understood that the embodiment of the invention described above and shown in the drawings is to be regarded as a non-limiting example only and that it may be modified in many ways within the scope of the patent claims.

The invention claimed is:

1. A casing for a pen-type injector having a tubular housing containing a separate container of medicament, where the casing comprises:
   a first shell section comprising an opening configured to hold the pen-type injector;

a second shell section configured to attach to the first shell section to form a shell enclosing the pen-type injector except for a proximal end of the pen-type injector, wherein each of the first shell section and second shell section further comprises:

two longitudinal edges;

a cut-out located at a proximal end configured to form a central passage when the second shell section is attached to the first shell section, where the central passage is sized to permit the proximal end of the pen-type injector to protrude through the central passage;

two longitudinal contact surfaces located along the longitudinal edges; and a plurality of attachments located on the two longitudinal contact surfaces, wherein mating of a first set of attachments on the first shell section with a second set of attachments on the second shell section will interact to lock the shell sections to each other to form the shell, wherein the first shell section and the second shell section further comprise a longitudinal opening positioned such that each longitudinal opening will align with openings in an outer housing of the pen-type injector so as to permit a user to view a content of medicament located within the pen-type injector when the pen-type injector is positioned within the formed shell.

2. The casing of claim 1, wherein the plurality of attachments comprises a plurality of protrusions and a plurality of seats configured such that engagement of one of the protrusions with one of the seats forms a locking cooperation between the protrusion and the seat.

3. The casing of claim 2, wherein the plurality of protrusions equals the plurality of seats.

4. The casing of claim 2, wherein the each of the plurality of the protrusions comprises a inclined surface that cooperates and locks with an inclined surface on each of the plurality of seats.

5. The casing of claim 1 further comprising a removable cap that is configured for attachment to a proximal end of the formed shell, where when the removable cap is attached to the formed shell the central passage and the protruding proximal end of the pen-type injector is covered and closed.

6. The casing of claim 1, wherein the formed shell has a closed distal end.

7. The casing of claim 1, wherein each of the longitudinal openings is configured to accept a window.

8. The casing of claim 1, wherein the first shell section is larger than the second shell section.

9. The casing of claim 1, wherein the second shell section is configured as a closure element so that connecting the second shell section to the first shell section when the pen-type injector is positioned within an opening in the first shell section will form the shell around the pen-type injector.

10. The casing of claim 1, wherein each shell section has fixation elements on an inner surface that contact and fixate with the pen-type injector within the formed shell.

11. The casing of claim 1, wherein each shell section further comprises an inner contact surface located on an inner surface.

12. An assembly comprising:

the casing according to claim 1; and a pen-type injector comprising a tubular housing configured as a manual or automatic device and as a disposable or reusable device that allows a user to inject a single dose or multiple doses of a medicament through a delivery member attached to a proximal end of a medicament container located within the tubular housing, wherein the casing further comprises a removable cap that is configured for attachment to a proximal end of the formed shell, where when the removable cap is attached to the formed shell the central passage and the protruding proximal end of the pen-type injector is covered and closed.

13. The assembly of claim 12, wherein the shell comprises an elongated and generally tubular central interior terminating at an end wall at a distal end of the shell, where the central interior is configured in size to hide the pen-type injector within the shell when the pen-type injector is placed within the central interior such that a proximal end of the pen-type injector extends through the central passage in the proximal end of the shell, and wherein the formed shell further comprises an inner surface comprising a fixation element configured to engage the tubular housing of the pen-type injector such that the injector cannot move relative to the shell when the injector is hidden within the central passage.

14. The assembly of claim 12 where the formed shell further comprises an opening configured to accept a window configured to permit a user to view the pen-type injector when the pen-type injector is hidden within the formed shell.

15. The assembly of claim 12, wherein the first shell section and the second shell section further comprise a longitudinal opening positioned such that each longitudinal opening will align with openings in an outer housing of the pen-type injector so as to permit a user to view a content of medicament located within the pen-type injector when the pen-type injector is positioned within the formed shell.

16. The assembly of claim 15, wherein the plurality of attachments comprises a plurality of protrusions and a plurality of seats configured such that engagement of one of the protrusions with one of the seats forms a locking cooperation between the protrusion and the seat.

17. The assembly of claim 16, wherein the plurality of protrusions equals the plurality of seats.

18. The assembly of claim 17, wherein the each of the plurality of the protrusions comprises a inclined surface that cooperates and locks with an inclined surface on each of the plurality of seats.

19. The assembly of claim 12, wherein the formed shell has a closed distal end.

* * * * *